United States Patent [19]

Garabedian

[11] Patent Number: Plant 7,159

[45] Date of Patent: Feb. 20, 1990

[54] PLUM TREE, "GAR-BELMONT"

[76] Inventor: John M. Garabedian, P.O. Box 7883, Fresno, Calif. 93747

[21] Appl. No.: 268,081

[22] Filed: Nov. 7, 1988

[51] Int. Cl.[4] ..... A01H 5/00

[52] U.S. Cl. ..... Plt./38

[58] Field of Search ..... Plt./38

*Primary Examiner*—Robert E. Bagwill

*Attorney, Agent, or Firm*—Worrel & Worrel

[57] ABSTRACT

A new and distinct variety of Plum Tree denominated varietally as "Gar-Belmont", and which is characterized as to novelty by a date of maturity for commercial harvesting and shipment of approximately June 1 through June 10 under the ecological conditions prevailing at Fresno, Calif. in the central part of the San Joaquin Valley of central California.

1 Drawing Sheet

BACKGROUND OF THE NEW VARIETY

The present invention relates to a new and distinct variety of Plum Tree, hereinafter denominated varietally as "Gar-Belmont" and more particularly to a plum tree which produces fruit which are somewhat remotely similar in their external appearance to the fruit produced by the Aleta Rose Plum Tree, U.S. Plant Pat. No. 5,231) and the Early Gar Rose Plum Tree, (U.S. Plant Pat. No. 5,453), but which is distinguished therefrom and characterized principally as to novelty by producing semi-freestone fruit which have a very dark red and attractive skin color and a pale yellow flesh color and which further is ripe for commercial harvesting and shipment approximately June 1 through June 10 under the ecological conditions prevailing in Fresno, Calif., the subject variety being ripe for commercial harvesting and shipment approximately two or three weeks before the Aleta Rose Plum Tree, and approximately five days after the Early Gar Rosa Plum Tree at the same Fresno County location.

As with all produce, the time of harvesting of plums greatly influences the price which they may bring at market. Fruit which can be marketed earlier, or in some instances later, than other well known commercial varieties can command greater prices when they are brought to market when competition is at a minimum. It is therefore desirable to provide a plum tree bearing fruit which have the commercially aesthetic appeal such as that presented by the Aleta Rose Plum Tree or alternatively the Early Gar Rosa Plum Tree, but which is ripe for harvesting and shipment approximately June 1 through June 10 under the ecological conditions currently prevailing in Fresno, Calif.

ORIGIN AND ASEXUAL REPRODUCTION OF THE NEW VARIETY

The present variety of plum tree was discovered as a chance open-pollinated seedling of unknown parentage developed from seeds which the inventor had procured from open cross-pollinated test trees which were then growing on his Ranch No. 1 which is located on the corner of Kings Canyon and Fowler Avenues in Fresno, Fresno County, Calif. The chance open-pollinated seedling, which was discovered in 1973, was noted at that time to have desirable characteristics and the inventor marked the subject tree for future observation. After evaluating the fruit produced by the chance open-pollinated seedling over a number of growing seasons, the applicant asexually reproduced the new variety by removing bud wood from the chance seedling, in 1977, and grafted this bud wood into existing mature plum trees or alternatively into Marianna rootstock. This first asexual reproduction which took place at the applicant's Ranch No. 10 which is located on the corner of Fowler and Belmont Avenues, in Fresno, Calif., resulted in progeny being produced which appeared to possess the same distinctive characteristics as the original chance seedling.

SUMMARY OF THE NEW VARIETY

The Plum Tree Gar-Belmont is noteworthy in producing fruit which are ripe for harvesting approximately June 1 through June 10 under the ecological conditions currently prevailing in Fresno, Calif., the subject variety maturing for harvesting and shipment approximately two or three weeks before the Aleta Rose Plum Tree (U.S. Plant Pat. No. 5,231) and approximately five days after the Early Gar Rosa Plum Tree (U.S. Plant Pat. No. 5,453) at approximately the same geographical location.

BRIEF DESCRIPTION OF THE DRAWINGS

The accompanying drawing is an illustration by photographic reproduction of several mature fruit of the subject variety sufficiently matured for harvesting and shipment, a twig bearing typical leaves displaying the upwardly and downwardly disposed surface colors thereof, and two fruit of the subject variety divided in the axial plane to illustrate the flesh and stone characteristics, all of the subject variety.

DETAILED DESCRIPTION

Referring more specifically to the pomological details of this new and distinct variety of plum tree, the following has been observed under the ecological conditions prevailing at the orchard of the inventor which is located on the corner of Belmont and Fowler Avenues in Fresno, Calif. All major color code designations are by reference to the Inter-Society Color Council, National Bureau of Standards. Common color names are also employed occasionally.

TREE

Generally:

*Size.*—Large as compared with other common plum cultivars growing in the San Joaquin Valley of central California.

*Vigor.*—Average and tender.

*Form.*—Spreading, open, and vase formed, depending upon pruning practices.

*Productivity.*—Productive.

*Regularity of bearing.*—Regular.

Trunk:

*Size.*—Average as compared with other common plum cultivars.

Surface texture.—Shaggy.

Branches:

*Color.*—A dull brown, this color is not particularly distinctive of the subject variety, however.

*Size.*—Generally—average.

*Surface texture.*—Shaggy.

*Lenticels — numbers.*—Average.

*Lenticels — size.*—Small.

LEAVES

Size:

*Generally.*—Average as compared with other common plum cultivars.

*Average length.*—Approximately 11.6 cm.

*Average width.*—Approximately 5.6 cm.

Shape:

*Generally.*—Ovate.

Apex:

*Shape.*—Acute.

Color:

*Upwardly disposed surfaces.*—Dark green, (125. m. 01 G.).

*Downwardly disposed surfaces.*—A pale green, (120. m. Y G).

Surface texture: Glabrous.

Marginal form: The variety is considered finely serrate.

Petiole:

*Average length.*—Approximately 15 mm.

*Average thickness.*—Approximately 1.4 mm.

Glands:

*Numbers.*—2 or 3 small glands are evident.

*Position.*—Alternate.

*Size.*—Small.

Color.—Red; this color is not particularly distinctive of the variety, however.

Stipules:

*Numbers.*—Two stipules can usually be found.

FLOWER BUDS

Generally: Small, short, and tender.

Shape: Conic, and free.

Pubescence: The variety is only minimally pubescent.

FLOWERS

Date of bloom:

*Generally.*—The new variety of Plum Tree, Gar-Belmont, blooms at approximately the same time of the season as the Early Gar Rosa Plum Tree (U.S. Plant Pat. No. 5,453) at the above-identified Fresno County location.

*Date of first bloom.*—In 1988, first bloom was observed on February 20.

*Date of full bloom.*—In 1988, full bloom was observed on February 26.

Blossoms:

*Size.*—Average as compared with other common plum cultivars.

Petals:

*Color.*—Pink, this color is not particularly distinctive of the subject variety, however.

FRUIT

Maturity when described: Ripe for harvesting and shipment approximately June 1 through June 10 under the ecological conditions prevailing at the orchard of the inventor in Fresno County, Calif.

Size:

*Generally.*—Average.

Uniformity: Uniform.

Average axial diameter: Approximately 50.4 mm.

Average diameter transverse and in the suture plane: Approximately 57.7 mm.

Average diameter transverse and at right angles to the suture plane: Approximately 59.5 mm.

Form:

*Uniformity.*—Symmetrically compressed. However, the variety does appear occasionally roundish.

Suture:

*Generally.*—The suture appears as an inconspicuous line which extends from the apex to the stem cavity.

Ventral surface:

*Shape.*—Rounded.

Stem cavity:

*Shape.*—Circular and flaring.

*Depth.*—Approximately 7.2 mm.

*Width.*—Approximately 6.9 mm.

Base:

*Shape.*—Rounded.

Apex:

*Shape.*—Rounded and truncate. Further, the apex may appear slightly depressed.

Skin:

*Thickness.*—Average and occasionally thin, tender.

Tenacious to flesh: Yes.

Tendency to crack: Not observed in the dry season.

Down:

Quantity.—Wanting.

Skin color:

*Very dark red,* (17 v.d. Red).

Flesh color: Variable, a cream color to pale yellow, (89 p.Y to 104 P. g Y).

Amygdalin:

*Quantity.*—Wanting.

Juice production: Average.

Flesh texture: Firm and melting at full commercial maturity.

Fibers:

*Generally.*—Few, fine, and tender.

Ripening: Even.

Flavor:

*Generally.*—Considered mild to subacid.

Aroma: Wanting.

Eating quality: Good.

STONE

Attachment: The subject variety Gar-Belmont is considered a semi-freestone fruit. More particularly, the stone adheres to the flesh along the suture and about the dorsal and ventral edges thereof.

Size:

*Generally.*—Considered medium to large.

*Average length.*—Approximately 21.9 mm.

*Average length.*—Approximately 20.2 mm.

*Average thickness.*—Approximately 10.9 mm.

Form:

*Generally.*—Oval.

Base:

*Shape.*—Straight.

Hilum:

*Shape.*—Narrow and oval.

Apex:

*Shape.*—Rounded.

Sides: Equal and slightly curved.

Surface texture: Irregularly furrowed along the ventral edge.

Ventral edge:

*Generally.*—Thin.

Dorsal edge: Narrow.

Stone:

Color.—Orange-yellow (73 p.o y).

Tendency to split: Not observed.

Use: The subject variety Gar-Belmont is considered a fresh market plum.

Keeping quality: Average.

Resistance to inspects and disease: Average as compared with other plum cultivars common in the San Joaquin Valley of central California.

Shipping quality: Average.

Although the new variety of plum tree Gar-Belmont possesses the described characteristics when grown under the ecological conditions prevailing in Fresno, Calif., in the central part of the San Joaquin Valley, it is to be understood that variations of the usual magnitude and characteristics incident to changes in growing conditions, fertilization, pruning and pest control are to be expected.

Having thus described and illustrated my new variety of plum tree, what is new and desired to be secured by Letters Patent is:

1. A new and distinct variety of plum tree substantially as illustrated and described and which is somewhat similar to the Aleta Rose Plum Tree (U.S. Plant Pat. No. 5,231) and the Early Gar Rosa Plum Tree (U.S. Plant Pat. No. 5,453), but which is distinguished therefrom and characterized principally as to novelty by producing fruit which are ripe for harvesting and shipment approximately June 1 through June 10 under the ecological conditions prevailing in Fresno, Calif., the subject variety producing fruit which are ripe for harvesting and shipment approximately two or three weeks before the Aleta Rose Plum Tree and approximately five days after the Early Gar Rosa Plum Tree at the same geographical location.

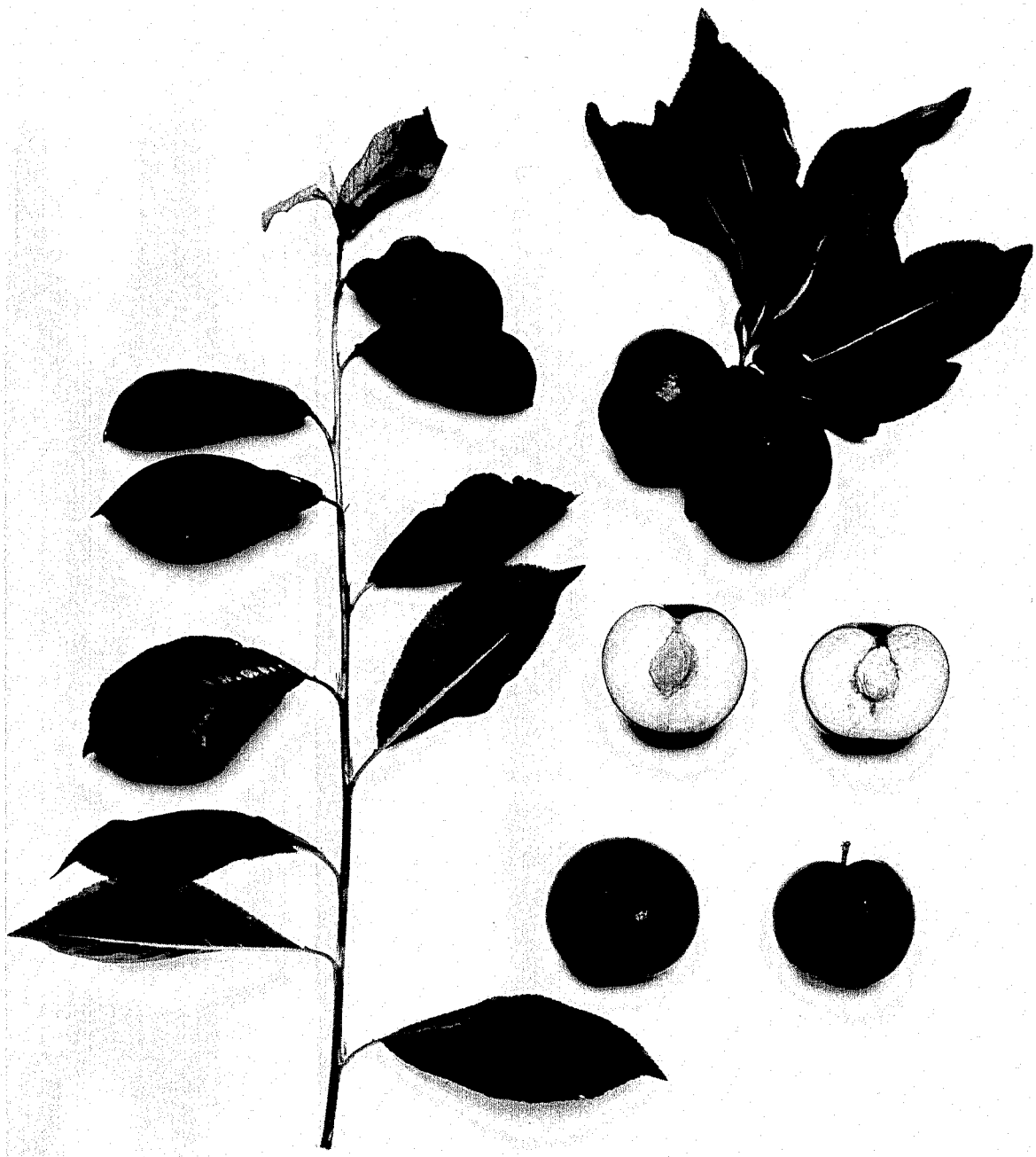

* * * * *